(12) United States Patent
Koch et al.

(10) Patent No.: US 12,093,776 B2
(45) Date of Patent: Sep. 17, 2024

(54) METHOD FOR CAPTURING COMPUTER-READABLE CODES, READING DEVICE AND READING SYSTEM

(71) Applicant: Aesculap AG, Tuttlingen (DE)

(72) Inventors: Jan Koch, Tuttlingen (DE); Mirco Vitr, Aachen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/039,142

(22) PCT Filed: Nov. 30, 2021

(86) PCT No.: PCT/EP2021/083602
§ 371 (c)(1),
(2) Date: May 26, 2023

(87) PCT Pub. No.: WO2022/112606
PCT Pub. Date: Jun. 2, 2022

(65) Prior Publication Data
US 2023/0419059 A1  Dec. 28, 2023

(30) Foreign Application Priority Data

Nov. 30, 2020  (EP) .................................... 20210781

(51) Int. Cl.
*G06K 7/10* (2006.01)
*G06K 7/14* (2006.01)

(52) U.S. Cl.
CPC ....... *G06K 7/10722* (2013.01); *G06K 7/1413* (2013.01); *G06K 7/1417* (2013.01)

(58) Field of Classification Search
CPC . G06K 7/10722; G06K 7/1413; G06K 7/1417
See application file for complete search history.

(56) References Cited

U.S. PATENT DOCUMENTS 9,495,658 B2  11/2016  Hookom et al.
2011/0215146 A1  9/2011  Shams
(Continued)

FOREIGN PATENT DOCUMENTS

| CN | 106295437 A | 1/2017 |
| DE | 4107020 A1 | 9/1992 |
| JP | 2016212603 A | 12/2016 |

OTHER PUBLICATIONS

Search Report received in International Application No. PCT/EP2021/083602 dated Feb. 25, 2022, 4 pages.
(Continued)

*Primary Examiner* — Laura A Gudorf
(74) *Attorney, Agent, or Firm* — Culhane PLLC; Christopher A. Rothe

(57) ABSTRACT

A reading device, system, storage medium and method for capturing computer-readable codes of a medical product or packaging. The method includes: capturing an image of the product or packaging, extracting first and second computer-readable code, interpreting code data, retrieving a product-ID and further product information from the code data, determining if relevant information is included in the information of the captured code and/or a linked database, selecting the second code as a relevant code if retrieved information of the first code is fully included in the retrieved information of the second code, or selecting the first and second codes as the relevant code if each code includes relevant information, transmitting a code marker for each code to a displaying device, and displaying an overlay image with the captured image and a marking of the code to provide an improved overview of the computer-readable codes to the user.

21 Claims, 8 Drawing Sheets

(56) References Cited

U.S. PATENT DOCUMENTS

2015/0178523 A1\* 6/2015 Gelay ................ G06K 7/1095
2016/0171258 A1 6/2016 Reitstaetter

OTHER PUBLICATIONS

Written Opinion received in International Application No. PCT/EP2021/083602 dated Feb. 25, 2022, 9 pages.

\* cited by examiner

| AI | Description | Short Name |
|---|---|---|
| 00 | Serial Shipping Container Code | SSCC |
| 01 | Global Trade Item Number | GTIN |
| 02 | GTIN of trade items contained in a logistic unit | CONTENT |
| 10 | Batch or lot number | BATCH/LOT |
| 11 | Production date (YYMMDD) | PROD DATE |
| 12 | Due date for amount on payment slip (YYMMDD) | DUE DATE |
| 13 | Packaging date (YYMMDD) | PACK DATE |
| 15 | Best before date (YYMMDD) | BEST BEFORE or BEST BY |
| 17 | Expiration date (YYMMDD) | USE BY or EXPIRY |
| 20 | Internal product variant | VARIANT |
| 21 | Serial number | SERIAL |
| 22 | Consumer product variant | CPV |
| 241 | Customer part number | CUST. PART NO. |
| 242 | Made-to-Order variation number | MTO VARIANT |
| 250 | Secondary serial number | SECONDARYSERIAL |
| 251 | Reference to source entity | REF. TO SOURCE |
| 253 | Global Document Type Identifier | GDTI |
| 255 | Global Coupon Number | GCN |
| 400 | Customer's purchase order number | ORDER NUMBER |
| 401 | Global Identifier Number for Consignment | GINC |
| 402 | Global Shipment Identification Number | GSIN |
| 7003 | Expiration date and time (YYMMDDHHMM) | EXPIRY TIME |
| 8003 | Global Returnable Asset Identifier | GRAI |
| 8004 | Global Individual Asset Identifier | GIAI |
| 8008 | Date and time of production (YYMMDDHHMMSS) | PROD TIME |
| 8013 | Global Model Number (GMN) | GMN |
| 8017 | Global Service Relation Number | GSRN - PROVIDER |
| 8018 | Global Service Relation Number | GSRN - RECIPIENT |
| 8020 | Payment slip reference number | REF NO. |

Fig. 3

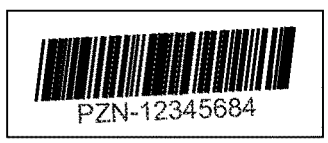
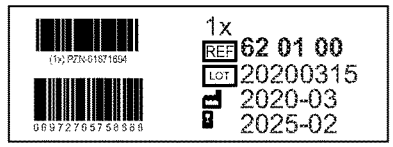
Fig. 4a          Fig. 4b          Fig. 4d
Fig. 4c          Fig. 4e          Fig. 4f
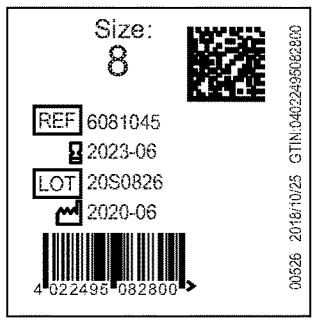
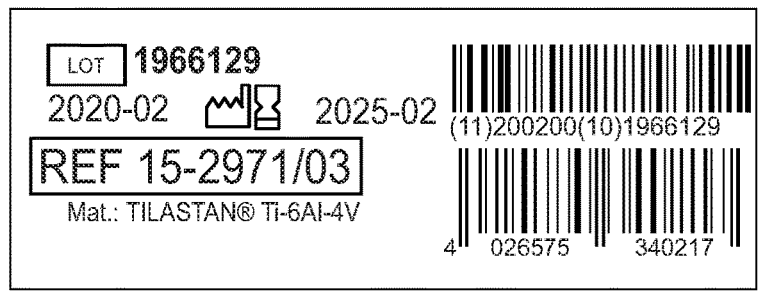
Fig. 4g          Fig. 4h
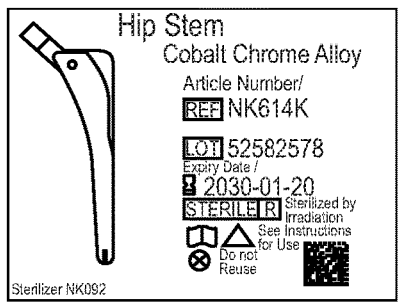
Fig. 4i          Fig. 4j
Fig. 4k

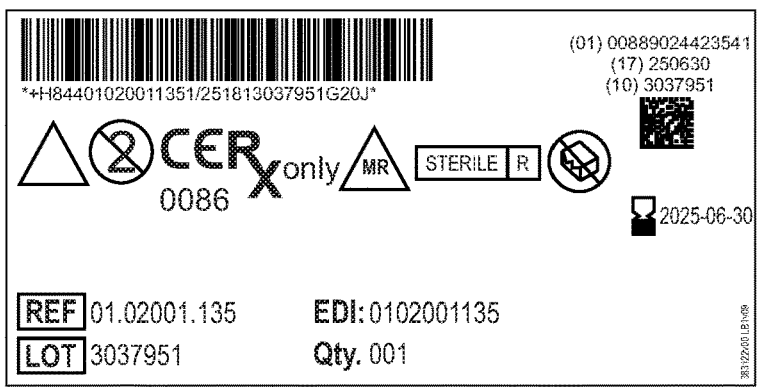
Fig. 4l
Fig. 4n
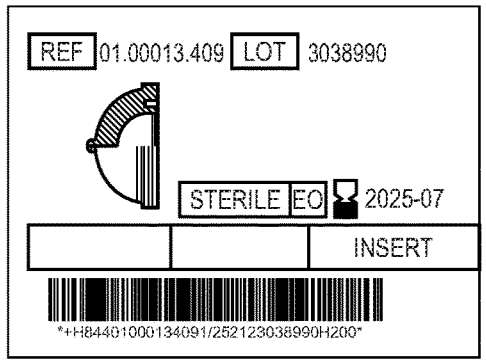
Fig. 4m
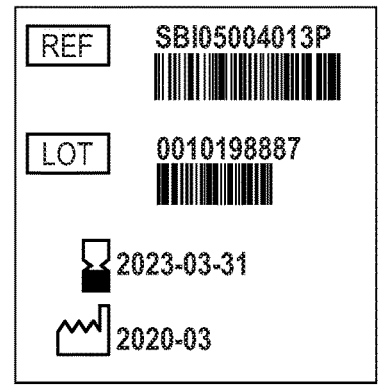
Fig. 4o
Fig. 4p
Fig. 4q
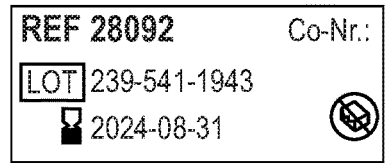
Fig. 4r

Fig. 4s       Fig. 4t       Fig. 4u
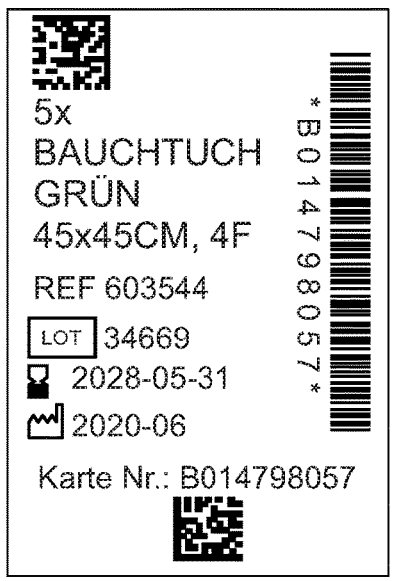
Fig. 4w
Fig. 4v
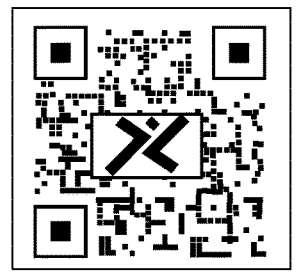
Fig. 4x

METHOD FOR CAPTURING COMPUTER-READABLE CODES, READING DEVICE AND READING SYSTEM

CROSS-REFERENCE TO RELATED APPLICATIONS

This application is the United States national phase entry of International Application No. PCT/EP2021/083602, filed Nov. 30, 2021, and claims priority to European Application No. 20210781.9, filed Nov. 30, 2020. The contents of International Application No. PCT/EP2021/083602 and European Application No. 20210781.9 are incorporated by reference herein in their entireties.

FIELD

The present disclosure relates to a method for capturing multiple computer-readable codes, preferably barcodes and/or 2D-codes, of a medical product or a packaging of a medical product for assisting a user. Besides, the present disclosure relates to a reading device, a reading system, and a computer-readable storage medium. In particular, the disclosure can be used to process the information scanned from medical products a packaging (items) with more than one computer-readable code, preferably more than one barcode, and to determine the information contained therein. Preferably, the scanner can determine relevant information in dependence of the intended use. One field of usage is the processing and documentation of medical devices.

BACKGROUND

Keeping track and documenting the medical devices as a medical product that are used in connection with a patient or a medical procedure for a patient is essential, in order to be able to trace back the devices, wherein a device can be any type of medical product as well, in case of an infection or device recall. It is necessary to be able to determine which specific items (medical product), including their lot or serial number information, have been employed, e.g. implanted or used, in context with a patient. A lot number can also be called batch number sometimes.

Currently manual documentation is common, which includes removing detachable stickers from devices. Frequently these stickers are collected by the personnel in one way or the other. For example, it is known to attach the stickers to the scrubs being worn during the procedure.

Later, at a workstation, which is used for documentation purposes, the stickers are removed and attached onto forms or paper, which can then in turn be archived and/or digitalized.

Disadvantageously, some devices do not have stickers. In this case, the information, for example a lot, can be printed on the item, the items packaging (packaging of a medical product), or the packaging of a set of items. These items are prone to be forgotten and thus missing in the documentation later on.

In the systems currently used in a hospital, for example hospital information system (HIS), hospital management software or hospital management system (HMS), laboratory information system (LIS), policy and procedure management system, radiology information system (RIS), picture archiving and communication system (PACS), enterprise resource planning (ERP) system, or the like, the usage of medical items for a patient can be digitally documented. Often a barcode scanner is employed to collect the information from the collected stickers.

Two primary standards have prevailed for medical devices, GS1 (global standards 1), e.g. GTIN (global trade item number), and HIBC (health industry barcode) systems. For certain devices, also the Pharmaceutical central number (PZN, for German "Pharmazentralnummer") is used. In order to relate the correct item to the barcode that is scanned, a database has to be maintained containing master data of all items possibly used. Therefore, the information system used needs a materials management block or an interface between the information system and a material management software is necessary.

As an exemplary research has shown, about 27 percent of the data sets of implants that were scanned in a hospital were not maintained correctly, i.e. the GTIN was missing. Consequently, the barcodes could be scanned, but not processed correctly. In such cases, the user is merely shown an error message, with no possibility to remedy the data other than to enter the missing data manually.

This is in particular detrimental, since—at least in some countries—implants, like knee and hip replacement implants need to be documented on a legal basis. With the manual entry of implant data after scanning, human error can contribute to a poor quality of the data in the system. Erroneous data can also lead to claim for damages; therefore having a correct database of all items used is very desirable.

Further, some devices or lots have more than one barcode on them. The manufacturers of medical devices have a certain liberty on how to code the relevant information on their devices. In particular, the GS1 standard can be interpreted differently, leading to inconsistent presentation of information on the devices from different manufacturers. It would be desirable that all relevant information is present in one scannable element, preferably a data matrix code or a similar code. A data matrix is 2D code, as shown in FIG. 2a, which can require less surface than a conventional barcode. Some data matrix principles are described in DE 41 07 020 A1. With a data matrix of the size 48 rows and 48 columns, which is a common size of data matrixes, 348 numerical or 259 alphanumerical characters can be indicated. Depending on the printed resolution, a 48×48 data matrix would be of the size 10×10 mm up to 20×20 mm. According to the defining standard ECC 200 currently used, the largest data matrix for common use is 144×144, which can hold up to 3116 numerical or 2355 alphanumerical characters.

In comparison to that, with a conventional barcode on a book, the books international standard book number (ISBN), which is a 13-digit number, is indicated. Such a barcode is shown in FIG. 2b.

Relevant information for documentation of medical devices include the GTIN, an expiration date, and a lot or serial number. However, in reality, this information, and possibly further information, which is irrelevant for the documentation, is often placed on the medical devices, as can be seen in FIGS. 2c to 2g, showing real-world examples. In FIG. 2c the lowest of three barcodes would contain all relevant information. In FIG. 2d the lower of two data matrixes would be the correct one to be scanned for all relevant information. Users are often confused and overwhelmed, resulting in unnecessary scanning procedures and an increased probability for errors leading to incorrect data sets. Other devices do not have a single code item that contains all relevant information, but several barcodes or data matrixes. Scanning with prior art techniques results in an incomplete documentation in these cases. FIG. 2e shows an example, where the lower barcode contains the GTIN (i.e.

value after indicator field "(01)") and the expiration data (i.e. value after indicator field "(17)") while the upper barcode contains the lot number (i.e. value after indicator field "(10)").

While scanning barcodes, the user has to observe a certain sequence of scanning of scanning for the information system to process the scanned data correctly. The current procedure required that the lot number must be scanned first, in order to indicate to the information system, that further information will follow in addition to the GTIN. If the GTIN is scanned first, the lot number will be joined with the following GTIN. The documentation would be erroneous, and there is no warning or other indication to the user. Current scanning devices require skilled and knowledgeable workers that are aware of these issues and scan codes in the correct sequence. However, the room for error is high in the current system.

Many scanners (as a capturing device) are designed to detect data matrix codes by not employing a single line target ray highlighting the computer-readable code, but rather to scan in a rectangular area. If more than one code is within this area, the scanner has to determine which code to scan and evaluate first. Experienced personnel is known to cover the codes that must not be scanned or not be scanned at first, such that the scanning efficiency is improved. That means, the user covers the code containing the GTIN and scan the lot number first. However, the indicator fields of the GS1 standard are not commonly known, and different fields can be used to indicate similar information. The GS1 standard known more than 500 different so-called application identifiers. FIG. 3 shows an excerpt of GS1 application identifiers. Also, some users are mistaken to always scan the longer code first or to scan the codes in vertical order, while in reality, neither the length nor the position divulge any of the contents of the codes, instead the user would be required to look for the application identifier "(10)", which is in the upper code in FIG. 2f but in the lower code in FIG. 2g.

For example, the US 2016/0 171 258 A1 discloses a system for detecting and processing codes of medical products. A code is scanned and linked to a central module with a database. Product information of the medical product is retrieved from the code or the database. The user receives a feedback if the necessary information has been read/captured or if the user needs to scan further codes. It is only possible to scan one code at the time and determine if the one code contains the necessary information.

A barcode scanner and a recognition device is known from JP 2016-212 603 A. The barcode scanner scans one or more codes and the recognition device interprets the codes. The recognition device links the code data to a database and counts how often a code was already read. Thereby, the recognition device is able to avoid that the same code is scanned multiple times. The recognition device is also able to determine if a code is two-staged and when this is the case, is able to read two codes in the right order/sequence.

It is thus already known from the prior art to scan computer-readable codes and determine if necessary information is present. However, existing solutions are not able to indicate to the user which code is the best code from a number of scanned codes. Further, the existing solutions are not able to combine the product information from multiple codes to retrieve the necessary information.

SUMMARY

It is therefore an object of the present disclosure to be able to capture multiple computer-readable codes and to provide feedback to a user about the availability of necessary product data/information in the codes and about the relevance of the captured codes.

The present disclosure relates to a method for capturing, preferably scanning, multiple computer-readable codes, preferably barcodes and/or 2D-codes, of a medical product or a packaging of a medical product for assisting a user. The method comprises the following steps: capturing, preferably scanning, an image of the medical product or its packaging having the codes with a capturing device, preferably a smartphone having a camera, and extracting/identifying at least a first and a second computer-readable code in the captured image. Code data of the captured codes is interpreted/decoded by an interpretation device and information of at least a product-ID/product identifier and further product information, preferably an expiry date and/or a lot number, are retrieved from the code data.

It can be understood that capturing or scanning of the image means that the user or a device takes a picture of the medical product or the packaging of the medical product, preferably with a camera such as a smartphone camera or scans the product or the packaging with a capturing device such as a camera.

Furthermore, it is to be understood that code data of the at least first and second computer-readable code can for example be a (digital) picture of the codes. If the capturing device is able to interpret the computer-readable codes, the capturing device can also send code data that is interpreted data of the codes.

It is to be understood that product information is information related to the medical product and includes for example the product-ID, an expiry data and a lot number. The product information can further contain more information about the medical product, such as a maximum transport or storage time for a vaccine for example.

Further, it is to be understood that interpreting of the code data means the retrieving of information from the computer-readable codes. For example, a code can be interpreted to identify the code as a GS1-standard code containing the product-ID wherein the product-ID is a number or a combination of numbers and letters can be read from the code.

The method according to the disclosure further comprises the steps: determining, based on the retrieved information, if a predefined set of relevant information for the medical product is included in the information of the captured code and/or a linked (master data-) database. Moreover, selecting the second code as a relevant code, if the retrieved information of the first code is fully included in the retrieved information of the second code, or selecting the first code and the second code as the relevant code, if each code includes at least one part of the information of the predefined set of relevant information.

It is to be understood that predefined relevant information is information related to the medical product that is required to be scanned and documented. The predefined relevant information can differ from the type of the medical product. For example an implant needs to be documented with a lot number, otherwise it would not fulfill the obligatory documentation requirement. The predefined relevant information can be defined for example by legal requirements, by the user or by different requirements such as hospital intern requirements.

The computer-readable code(s) is/are selected as the relevant code(s) when it/they contain the predefined set of relevant information. The relevant code can be only one code that contains all relevant information or can be a set of codes that contain the relevant information combined.

The method further comprises the steps: Transmitting, based on the result of the determining and on the result of the selecting, a code marker for each code to a displaying device; and displaying an overlay image with the captured image and, according to the code marker, a marking of the code for adding assisting visual information to the code in order to provide an improved overview of the computer-readable codes to the user.

The code marker is additional information that is "added" to the computer-readable codes. The additional information adds for example a statement to the codes if the code is a relevant code, an invalid code, or a code that is valid but does not include additional product information.

The overlay image is an image that contains the captured image with the computer-readable codes and according to the code marker, a marking of the code. The marking provides visual feedback about the code to the user. The marking can for example be a predetermined colored box around the code.

In other words, the capturing device may be adapted to scan one or multiple computer-readable codes like barcodes or 2D-codes. The capturing device identifies the computer-readable codes in the captured image and transmits the code data of the multiple codes from the capturing device to the interpretation device. The interpretation device interprets the barcode data. By doing so, the interpretation device retrieves the product information from the code data. The product information is information related to the medical product and are for example the product identifier, the lot number and the expiry date of the medical product. The interpretation device determines if the predefined relevant information is included in the product information of the relevant codes. The interpretation device also checks if missing product information is stored in the database. The interpretation device selects one code as the relevant code, if all product information of the other codes is also included in the one code. If there is not one code that includes all product information of the other codes, multiple codes can be the relevant codes. A relevant code is every code that adds new product information. Therefore, if multiple codes are the relevant codes, the information contained in the codes combines the predefined set of relevant information. The retrieved product information is stored in the (master data-) database. To sum up, the interpretation device determines if the product information of the captured contains the predefined relevant information, or if the predefined relevant information can be retrieved from the database instead. It is possible to combine product information from the code data and retrieved product information from the database to achieve the predefined relevant information.

The interpretation device transmits the code marker of the relevant code to the displaying device. The code marker adds additional information to the code. The displaying device displays the overlay image to the user. The overlay image contains the captured image and the marked relevant code or codes. The marking highlights the relevant code to the user and thus provide additional information to the user. According to the determination of the interpretation device, the marking of the relevant code is differently. If the determination of the interpretation device is positive, the relevant code may be simply marked. According to one embodiment, the color of the marking may be preferably green. Optionally, the user receives feedback that the scanning is complete. However, if the determination of the interpretation device is negative, the overlay image further comprises an alarm or a message for informing the user that relevant information is incomplete. The relevant code is still marked/highlighted, as it contains product information. However, the relevant code may be in this case highlighted in red or orange.

Expressed differently, the present disclosure in particular relates to a method for data acquisition of consumption of an item (medical product) of medical material in an activity (like a surgery) from computer-readable codes, preferably barcodes, in an image containing one or more barcodes, the method may comprise the steps: acquiring barcode information of at least one computer-readable code, preferably barcode, wherein each computer-readable code information comprises device identifier information (product-ID), production identifier information (for example lot number or expiry date), and computer-readable code, preferably barcode, type information, retrieving additional item information from a database on the basis of the device identifier information (product-ID), production identifier information (for example lot number or expiry date), and barcode type information; determining, on the basis of the device identifier information, the production identifier information, the barcode type information, and the additional item information, whether a predetermined required set of information (predefined set of relevant information) for the item is present in the computer-readable codes, and if yes, the minimal set of computer-readable codes, preferably barcodes, that contain the predetermined required set of information for the item, according to predetermined rules, transmitting marking information (code marker) based on the result of the determining for displaying the image and providing marking for the barcodes contained in the image (overlay image); and storing the predetermined required set of information for the item in association with the activity in a memory.

The method in accordance with the present disclosure has the following advantages. Simply put, the method chooses the best computer-readable code from a set of multiple computer-readable codes. Preferably, the best code is be highlighted for the user and additional information is provided. Therefore, the user knows exactly which code from a number of codes is the best one. If there is not one single code on the medical product or packaging that contains all relevant information, product information from multiple codes can be combined to collect the relevant information. The main problem that a code containing the product identifier is scanned before a code containing the lot number and the lot number is linked to the wrong product is avoided. In the present disclosure, multiple computer-readable codes can be scanned simultaneously making sure that the codes scanned belong to the same medical product. If information is missing in the scanned codes, the user receives an alarm or warning. It is also possible to scan a single code. The user receives a feedback if the single code contains all relevant information or not. Further, reordering of medical products to refill stock to a predetermined number of items can easily be automated, if the information system is ensured to have correct usage information in real time.

Preferably, the code marker may contain an information that refers to an overlay color and/or a shape around the barcode and/or a text and/or a symbol at or near the respective code. The code marker can for example be a box around the code. The code marker can have different colors for differ different codes, based on the result of the determination. For example, relevant codes could be marked green. Codes that are readable but do not include further product information could be marked orange or yellow. Invalid codes could be marked red. The code marker with the different information about the code assists the user.

Based on the marking of the code, the user can easily distinguish which codes are relevant or not. The user is also informed, if the captured set of codes contains the predefined set of relevant information and alarmed if the captured codes do not contain the predefined set of relevant information. The user can learn for the future which codes are relevant from the marking of the codes.

In other words, in particular a marking information (code marker) can refer to one of an overlay color, a shape around the computer-readable code, preferably barcode, text, a number, and/or a symbol at or near the code, and/or wherein different markings can be used for one or more of the codes which have been determined to comprise the predetermined required set of information for the item; one or more of the codes, if the predetermined required set of information for the item is not determined to be present in the codes; one or more of the codes which have been determined to be invalid; one or more of the codes which have been determined to be valid, but no associated additional item information could be retrieved from the database; and/or one or more of the codes which have been not been used in the minimal set of codes.

Preferably, the method further comprises the steps: adding the product information to the (master data-) database by the interpretation device; and determining, by the interpretation device, if the database contains the predefined required information, preferably the product-ID, an expiry date and a lot number. Further, the method comprises: assigning, if the determination was negative, an alarm or a message to the code marker; and displaying the overlay image with the alarm or message assigned to the code by the displaying device to the user.

In other words, the product information that is retrieved from the code data may be stored in the (master data-) database. After the information is added to the database, the interpretation device determines, if the predefined required information is present in the database. Based on the result of the determination, the code marker that is transmitted to the displaying device differs. If the determination is positive, the code marker includes information which codes are relevant. The relevant codes are highlighted in the overlay image. However, if the determination was negative, the code marker includes the alarm or message. The alarm or message is shown in the overlay image to the user to inform the user that not all predefined required information is present in the codes.

Preferably, the interpretation device stores the retrieved product information in the database and determines if the database contains the predefined required information. The database is complete after storing of the product information if the retrieved product information contains the predefined required information or if required information is already stored in the database. If the interpretation device determines that the predefined required information is not included in neither the product information nor the database, the user may receive an alarm or a message by the displaying device. The interpretation device can check if the relevant information is contained in the captured codes. If the relevant information is not contained in the captured codes, the interpretation device checks if it is possible to extract the information from the database. If it is not possible to extract the information from either the codes or the database, the user receives feedback that the required information is not present.

Preferably, the method further comprises the step: assigning, if one or more of the codes have been determined to comprise the predefined set of relevant information for the medical product, a green box surrounding the respective code to the respective code marker. In a further step, displaying the overlay image with green boxes surrounding the respective codes by the displaying device to the user. When one or more captured codes contain the predefined set of relevant information, the codes are determined to be the relevant codes. The relevant code or codes are marked with a green box in the overlay image. The user can easily see that one or more relevant codes are present and that the scanning is complete.

Preferably, the method further comprises the steps: assigning, if one or more of the codes have been determined invalid to be not conform with a supported standard for computer-readable codes, a hiding flag for hiding the respective code; displaying the overlay image in which the respective code is masked/hidden/faded out. Irrelevant codes or codes that are not standard codes can be hidden in the overlay image. The user is not distracted from the irrelevant codes and can focus on the relevant codes. The user might learn for the future, which codes are relevant or not.

Preferably, the method further comprises the steps: connecting the retrieved product-ID with the (master data-) database by storing the product-ID in the database or by linking the product-ID of the code data of the relevant code to an existing correlated product-ID of the database by the interpretation device. Further, the method comprises the steps: adding the further product information data to the database of the product-ID by the interpretation device; and determining by the interpretation device, if the database of the connected product-ID contains the predefined required information, preferably an expiry date and/or a lot number. After scanning of the code, the medical product is linked to the (master data-) database. The interpretation device determines if information can be retrieved from the database. The information which product information is required for the predefined set of relevant information can also be retrieved from the database. By retrieving product information from the database, the predefined set of relevant information can be completed even if not all required information is included in the captured codes.

Preferably, the method further comprises: assigning at least a part of the retrieved information of the at least first and/or second code to the code marker of the respective code; and displaying the part of the retrieved information in the overlay image next to the code in order to assist the user with further information regarding the medical product. The code marker might include information about the information that is stored in the code. That might be the information that a code contains the product identifier. The displayed overlay image can contain a marker next to the code, that the code contains the product identifier. The product identifier that is a number can also be displayed next to the code. The user instantly sees which information each respective code contains. The user might also learn for the future which information is stored in the single codes. Using the additional information the user might learn the identifier of the codes.

The objective of the present disclosure is further solved by a reading device for capturing multiple computer-readable codes of a medical product or a packaging of a medical product for assisting a user. The reading device comprises: a capturing device configured to capture an image of the medical product or its packaging having the codes and to extract at least the first and the second computer-readable code in the captured image.

Further, the reading device comprises an interpretation device. The interpretation device is configured to interpret the code data and retrieve information of at least a product- ID and further product information from the code data. The interpretation device is further configured to determine, on the basis of the retrieved information, if a predefined set of relevant information for the medical product is included in the information of the captured code and/or a linked (master data-) database that is stored in a storage unit of the reading device or in a storage unit of a server. The interpretation device is further configured to select the second code as a relevant code, if the information of the code data of the first code is fully included in the information of the code data of the second code; or to select the first code and the second code as the relevant code, if each code includes at least one part of the information of the predefined set of relevant information.

A code marker for each code is transmitted to a displaying device, based on the result of the determining and on the result of the selecting. The reading device further comprises the displaying device configured to display an overlay image with the captured image and, according to the code marker, a marking of the code for adding assisting visual information to the code in order to provide an improved overview of the computer-readable codes to the user.

The reading device comprises the capturing device, the interpretation device and the displaying device. The capturing device is preferably a smartphone with a camera and is configured to take a picture of the medical product or scan the codes. The interpretation device is configured to determine if the required set of relevant information is present in the captured codes and/or the database. The interpretation device further selects the relevant codes and transmits the at least one code marker for the respective code(s) to the displaying device. The displaying device displays the overlay image consisting of the captured image and the information of the code marker embedded in the overlay image to the user.

In other words the present disclosure preferably provides a data evaluator (for example a reading device) for data acquisition of consumption of an item of medical material (a medical product) in an activity (surgery) from computer-readable codes, preferably barcodes in an image containing one or more codes. The data evaluator comprises an acquiring portion (capturing device), configured to acquire code information of at least one computer-readable code, preferably barcode, wherein each code information comprises device identifier information, production identifier information, and code type information, a retrieving portion (interpretation device), configured to retrieve additional item information from a database on the basis of the device identifier information, production identifier information, and code type information; a determining portion (interpretation device), configured to determine on the basis of the device identifier information, the production identifier information, the code type information, and the additional item information, whether a predetermined required set of information (predefined set of relevant information) for the item is present in the computer-readable codes, preferably barcodes, and if yes, the minimal set of computer-readable codes, preferably barcodes (relevant codes), that contain the predetermined required set of information for the item, according to predetermined rules; a transmitting portion, configured to transmit marking information (code marker) based on the result of the determining for displaying the image (overlay image) and providing marking for the computer-readable codes, preferably barcodes contained in the image; and a storing portion (database), configured to store the predetermined required set of information for the item in association with the activity in a memory.

The reading device comprises the following advantages. The reading device can scan multiple codes and can determine if the codes contain at least part of the predefined relevant information. The reading device can further determine a set of relevant codes that contains (at least part of) the predefined set of relevant information (especially in combination with stored remaining information of a database) and highlight them in the overlay image. Therefore, the reading device can chose the best code out of multiple codes or combine multiple codes to retrieve the required set of relevant data.

Preferably, the interpretation device is configured to determine that a first captured code is conform with the GS1-standard and that another GS1-standard barcode should be available to be captured, and if the determination is positive, the displaying device displays feedback to the user to capture another computer-readable code. Some medical products have more than one GS1-standard code. If it is known for a product to have more than one code and only one code is in the captured image, the user receives a feedback on the displaying device to scan the other code. Preferably, the user is asked to change the camera angle to capture more than one code.

Preferably, the interpretation device comprises text recognition and is configured to link computer-readable codes to a description that is not defined in the computer-readable code. Some products have computer-readable codes that do not tell which information is stored in them. The description is rather placed next to the codes in written text. It is useful that the interpretation device can read the text. The interpretation device can link the code with the text next to it. The interpretation device can read the text for example by optical character recognition (OCR) or with an artificial neural network.

Preferably, the interpretation device is configured to determine if the captured codes belong to a sterile material and if the determination is positive, the interpretation device retrieves additional information about the sterile material, preferably an expiry date, from the database. Sterile medical products or material is required to have an expiry date. If the interpretation device determines that a captured code belongs to a sterile medical product or material, it retrieves the additional information, preferably the expiry date, either from the captured code or from the database. The interpretation device determines if the material is expired or not and gives feedback to the user via the displaying device.

Preferably, the interpretation device is adapted to determine that not all information of the set of predefined relevant information is available and an electrically powered medical product is provided/used, the functionality of the medical product, preferably the power supply, is interrupted by the interpretation device and an alarm is displayed to the user by the displaying device. If the interpretation device determines that not all predefined relevant information is available for the electrically powered medical product, the interpretation device can interrupt the power supply of the electrically powered medical product. The interpretation device could alternatively display an alarm to the user via the displaying device.

Preferably, the interpretation device has a predefined set of selectable code markers stored in the storage unit, wherein the code marker contains an information that refers to an overlay color and/or a shape around the barcode and/or a text and/or a symbol at or near the respective code.

The present disclosure further relates to a reading system for capturing multiple computer-readable codes of a medical product or a packaging of a medical product for assisting a user. The reading system comprises at least one reading device according to one of the preceding aspects of the present disclosure as a client device, and a central server device having a storage with a (master) database, the server being connected with the at least one reading device for transferring data to and from the reading device. The reading system has one central module for data processing and multiple capturing devices connected to the central module. The central module provides a combined database for product information. If for example one of the capturing devices is not working, another capturing device can be used providing the same functionality and having access to the same database and stored product information.

Preferably, the step of determining may further comprises determining, on the basis of the device identifier information, the production identifier information, the barcode type information, and the additional item information, whether the item is associated with the activity. The activity is preferably a surgery or another medical operation.

Preferably, a different marking can be used for one or more barcodes which indicate that the item is not associated with the activity.

Preferably, the predetermined required set of information (predefined set of relevant information) for the item comprises one or more of a unique item number, a manufacturer identifier, a manufacturer's item number, a serial number, a lot number, and/or an expiration date.

Preferably, the additional item (medical product) information comprises the predetermined required set of information for the item and/or the predetermined required set of information for the item comprises one or more of a serial number, a lot number, and/or an expiration date.

Preferably, the method further comprises one or more of: acquiring the image; detecting the barcodes in the image; decoding the detected barcodes on the basis of barcode coding tables; interpreting the decoded barcodes on the basis of interpretation tables; and/or displaying the acquired image together with the markings.

Preferably, the method further comprises prompting a user and receiving additional input from the user, if at least one invalid (bar)code is determined, the predetermined required set of information for the item is not determined to be present in the (bar)codes, and/or if the method has terminated successfully.

Preferably, the step of displaying further comprises displaying interaction elements, preferably based on the barcode information and/or additional item information.

Preferably, the method is repeatedly performed processing a plurality of images, preferably after lapse of a predetermined time and/or a user confirmation.

Preferably, a marking information (code marker) can refer to one of an overlay color, a shape around the barcode, text, a number, and/or a symbol at or near the barcode, and/or wherein different markings can be used for one or more of the barcodes which have been determined to comprise the predetermined required set of information for the item; one or more of the barcodes, if the predetermined required set of information for the item is not determined to be present in the barcodes; one or more of the barcodes which have been determined to be invalid; one or more of the barcodes which have been determined to be valid, but no associated additional item information could be retrieved from the database; and/or one or more of the barcodes which have been not been used in the minimal set of barcodes.

Preferably, the determining portion (interpretation device) is further configured to determine on the basis of the device identifier information, the production identifier information, the barcode type information, and the additional item information, whether the item is associated with the activity.

Preferably, a different marking can be used for one or more barcodes which indicate that the item is not associated with the activity.

Preferably, the predetermined required set of information for the item comprises one or more of a unique item number, a manufacturer identifier, a manufacturer's item number, a serial number, a lot number, and/or an expiration date.

Preferably, the additional item information comprises the predetermined required set of information for the item; and/or wherein the predetermined required set of information for the item comprises one or more of a serial number, a lot number, and/or an expiration date.

Preferably, a data evaluator is provided comprising one or more of an acquiring portion, configured to acquire the image; a detecting portion, configured to detect the barcodes in the image; a decoding portion, configured to decode the detected barcodes on the basis of barcode coding tables; an interpreting portion, configured to interpret the decoded barcodes on the basis of interpretation tables; and/or a display portion, configured to display the acquired image together with the markings.

Preferably, the data evaluator further comprising an interaction portion, configured to prompt a user and receive additional input from the user, if at least one invalid barcode is determined, the predetermined required set of information for the item is not determined to be present in the barcodes, and/or if data acquisition from an image has terminated successfully.

Preferably, the data evaluator further comprising a display portion, configured to display interaction elements, preferably based on the barcode information and/or additional item information.

Preferably, the data evaluator is configured to successively process a plurality of images, preferably to proceed to a next image after lapse of a predetermined time and/or a user confirmation.

In addition, the present disclosure relates to a computer program product including a program for a processing device, comprising software code portions for performing the method according to the preceding aspects when the program is run on the processing device.

Preferably, the computer program product comprises a computer-readable medium on which the software code portions are stored, wherein the program is directly loadable into an internal memory of the processing device.

The present disclosure further relates to a computer-readable storage medium comprising instructions which, when executed by a computer, cause the computer to carry out the method according to one of the preceding aspects of the present disclosure.

The disclosure of the method for capturing computer-readable codes according to the present disclosure equally applies to the disclosure of the reading device of the present disclosure as well as vice versa.

BRIEF DESCRIPTION OF THE DRAWINGS

The present disclosure is explained in more detail below with reference to preferred embodiments with the aid of figures.

FIG. 3 is a list of GS1 standard application identifiers for a better understanding, FIGS. 4a to 4x show different product coding schemes for a better understanding.

The figures are schematic in nature and are intended only to aid understanding of the invention. Identical elements are provided with the same reference signs. The features of the various embodiments can be interchanged.

DETAILED DESCRIPTION

In the following, examples of the present disclosure will be described in detail using the accompanying descriptions.

Figure 1:
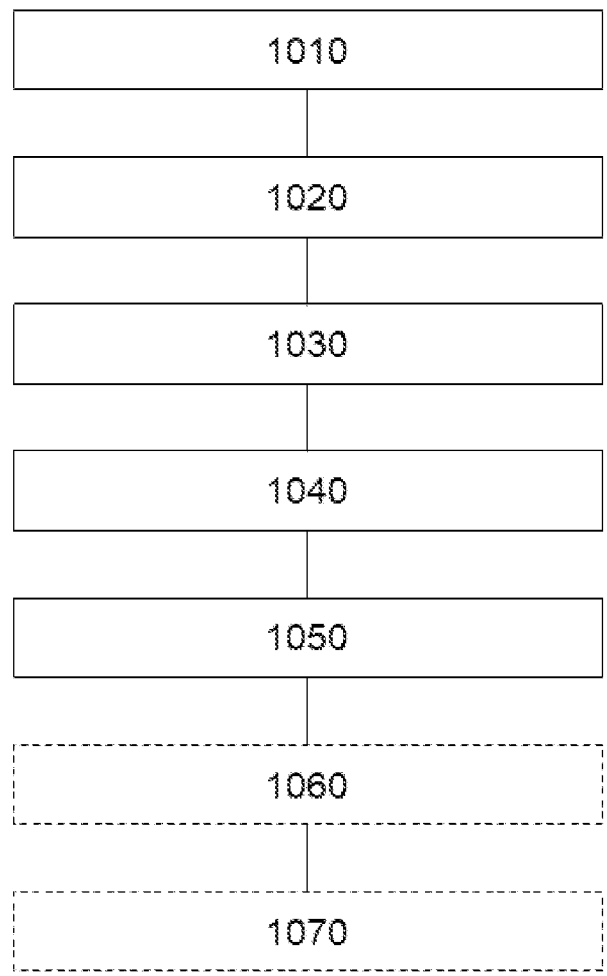
FIG. 1 shows a flow chart of a method of the disclosure according to one embodiment.

FIG. 1 shows a flowchart of a method 1000 for capturing multiple computer-readable codes of a medical product or a packaging of a medical product for assisting a user. In this embodiment, the method is adapted to capture barcodes and QR-codes. The method comprising the following steps.

In a first step 1010, the method is capturing an image of the medical product or its packaging having the codes by a camera as a capturing device 2.

In a second step 1020, the method is extracting at least a first barcode or QR-code and a second barcode or QR-code in the captured image.

Then, the method proceeds to step 1030, where the method performs Interpreting the code data by an interpretation device 4 and retrieving information of at least a product-ID and further product information in the form of an expiry date, from the code data.

In the step 1040, determining, on the basis of the retrieved information, if a predefined set of relevant information for the medical product is included in the information of the captured code and/or a linked database 8 is performed.

Step 1050 includes selecting the second code as a relevant code, if the retrieved information of the first code is fully included in the retrieved information of the second code, or selecting the first code and the second code as the relevant code, if each code includes at least one part of the information of the predefined set of relevant information.

When the determination and selecting is done, the process advances to step 1060 of transmitting, based on the result of the determining and on the result of the selecting, a code marker for each code to a displaying device 6.

Finally, the process advances to step 1070 of displaying an overlay image with the captured image and, according to the code marker, a marking of the code for adding assisting visual information to the code in order to provide an improved overview of the computer-readable codes to the user.

With such method, it is possible to add further information to the respective codes and to assist the user. The method especially is a method of augmented reality, where information of the real world is supplemented by information of the digital world thus beneficially adding the relevant information just where it is needed. The method is capable of capturing multiple computer-readable codes, and without the necessary knowledge of a user, automatically checks and interprets each computer-readable code and offers the user the result of the analysis of the data in form of additional information that is displayed to the user in order to facilitate the daily work, especially in a hospital. Further, since the selection is done automatically by the method, the safety of a patient is increased and the speed of a workflow in the hospital. Especially the method may be adapted to automatically add the information or at least part of the information that is included in the code, for example an expiry date, into an overlay image (real word-digital world) in order to show the user intuitively the necessary information. This as well eases a workload for a user that is now capable of concentrating to his specific tasks and fulfill them better. Besides a possibility of an error is minimized since the method is performed automatically by a machine and does not need any assistance or manual input by the user.

In particular, a specific QR-code or barcode that is the most informative and best code, is presented to the user, so that the user intuitively knows which barcode he has to focus on for example. Further, if more than one computer-readable-code contains the minimum set of relevant information, the user is shown exactly these barcodes. For example, if one barcode out of seven barcodes contains the information of an expiry date, the respective code out of the seven codes is highlighted and presented to the user that can now decide whether the expiry date is still valid or not or a warning message may be shown highlighting the barcode in a special color such as red in order to signal the user that the expiry date is already overdue. The user can then sort out the respective medical product. The method is providing the user with an advanced overview of relevant information of each specific case that is adaptable (advanced front-end).

Present scanning apparatuses on the other side are only able to acquire an image of an item that is placed before the scanner, and to detect and decode the barcodes thereon. Each barcode is decoded in dependence of its coding tables. For a barcode, the individual coded characters are coded in the geometry of the bars and spaces of the barcode. As an example, a Code 39 character consists of 5 bars and 4 spaces with 3 of them wide (for a binary value of 1) and 6 of them narrow (for a binary value of 0) for a total of nine elements. It encodes 43 different upper case alphabetic, numeric, graphic characters plus a space and has the capability to encode all 128 ASCII characters. An example of a decoding table, in this case for Code 39, can be seen in FIG. 5. The decoding portion processed the detected code and returns a sequence of decoded characters.

From a database data can be retrieved, configuring what a complete set of information is required to consist of. For example, for a medical device, a database can comprise that an expiration date is required, or with a vaccine, a transportation duration time must not be exceeded. Such constraints can be added from a database. In addition, changed requirements can be loaded in such manner, for example, while in transit, a recall information is added to the database, and thus the scanned item will be marked "expired" or "recall", thereby its usage can be avoided.

Optionally, the display can indicate to the user the code or codes that are eventually used, since they contain all the necessary information. This can be achieved, for example with a colored or monochrome overlay over the code(s), a colored or monochrome frame around the code(s), a symbol, e.g. a dot, star, or arrow next to the code(s) or any other visible indication. The remaining information can then be enriched with additional information selected from the master data of the database. Examples are manufacturer information, hospital item number, or item description.

However, devices are not always marked in such a way that information is contained in a single barcode or data matrix. The GS1 standard allows information to be distributed across multiple barcodes. When using a conventional barcode scanner, the user has to decide which code is to be scanned first or leave the decision to the barcode scanner. However, in those cases, errors in the documentation are likely, as detailed above.

With the present invention, it is possible to read several codes at the same time. If a complete set of information cannot be obtained from a single code, two or more codes can be combined in the manner described above.

The invention aims at making the documentation and assistance as easy as possible for the user. Therefore, the display could work with different colored brushes, e.g. overlays, so that users are made aware of and recognize different coding standards over time. The master data can be used to define how the article should be coded, which codes are expected and which information is to be documented. A brush is here a colored overlay indicating a marking of a certain area, like a highlighter brush on paper.

In the following some examples for medical device coding is detailed with reference to FIGS. 4a to 4x. It is noted that the same principles are applicable to devices in other fields as well.

As one example for medical devices, implants are detailed in the following. It is common for implants to bear coded information relating to the GTIN/LIC+PNC, expiry date, and lot or serial number. Known coding schemes for medical devices include:
Pharmaceutical central number (PZN, for German "Pharmazentralnummer") (shown in FIG. 4a)
European Article Number (EAN13+PZN) (shown in FIG. 4b)
EAN13 (shown in FIG. 4c)
GS1 (01) (shown in FIG. 4d)
GS1 (01)+GS1 (17/10) (shown in FIGS. 4e and 4f)
GS1 (01/17/10)+EAN 13 (shown in FIG. 4g)
GS1 (*/10)+EAN 13 (shown in FIG. 4h)
GS1 (01/17/10) (shown in FIGS. 4i and 4j)
GS1 (01/17/21) (shown in FIG. 4k)
GS1+HIBC (shown in FIG. 4l)
HIBC (shown in FIGS. 4m and 4n)
non standardized codes (shown in FIGS. 4o and 4p)
OCR in combination with barcodes (shown in FIG. 4q)
OCR only (shown in FIG. 4r)
sterile goods (shown in FIGS. 4s, 4t, and 4u)
Card number (shown in FIG. 4v)
Documentation or re-sterilized implants
eIFU, electronic instructions for use (shown in FIG. 4w)
QR-Code (shown in FIG. 4x)
validating the expiry date.

In the above, OCR, i.e. optical character recognition, comprises recognizing text comprised by individual letters, but also recognition of symbols, i.e. graphical symbols, for example the designation "LOT" in FIG. 4p or 4q or the hourglass symbol indicating an expiry date in FIG. 4q. Thus, this can also refer to image recognition and/or include machine learning to learn the meaning of commonly used symbols FIG. 4a shows the PZN. In Germany, drugs bear a pharmaceutical central number (PZN), in the European Union, a pharmacy product number, PPN, is used. The PZN or PPN standard has no priority for documenting and re-ordering of implants. However, in order to correctly track and re-fill hospital supplies, these codes need to be detected and interpreted correctly. The PZN should be marked differently, i.e. different color, shape, and/or symbol, from the GS1 code(s).

FIG. 4b shows a combination of EAN13+PZN. Since the PZN does not correspond to EAN13, both codes must be interpreted to identify the article. When creating new master data, the user should be asked whether the article contains other machine-readable codes. The joining of PZN and EAN13 is important so that the data can be correctly transmitted to materials management when ordering. An article that has been completely created in the master data should be identified via PZN or EAN13. The PZN should be marked differently, i.e. different color, shape, and/or symbol, from the GS1 code(s).

FIG. 4c shows the EAN13. For articles with an EAN13, the manual entry of an expiry date and lot or serial number is expected. When scanning and thereby creating new master data, the user should be asked whether the item contains other machine-readable codes and whether the expiry date and lot or serial number should be documented. Generally, manual input should be possible, but only required if it is necessary for the respective device. For example, manually recording the lot number for plasters is not justified for the device. In addition, documenting an implant without a lot number would not comply with the documentation requirement. This is also detailed below with context to other GS1 coding schemes.

FIG. 4d shows the GS1 with the identifier (01). There are devices with a barcode, that contain a GTIN with the identifier (01), but no other codes. While an EAN13 can be processed immediately, prior art scanners wait after scanning a GS1 (01) code for other codes to be scanned, until the user interacts, e.g. pressing a button "proceed", The master data in this case can indicate that no further codes are to be expected for this device. Manual entry of lot information can also be depending on the master data.

FIGS. 4e and 4f show GS1 with another identifier than the identifier (01). If it is known for a product to have more than one GS1 code, the user is encouraged to change the camera view to capture multiple codes.

FIG. 4g shows a GS1 code and EAN13 on the same packaging. When it is known for a product that a complete GS1 code exists next to the EAN13, the user is encouraged to scan the GS1 code. The EAN13 should not be processed in this case.

FIG. 4h shows an article with the EAN13 instead of the GS1 identifier (01). If it is defined in the master data that the product has a second code or a lot number must be scanned, the reading device does not process the EAN13 but waits for the lot number to be scanned.

FIGS. 4i to 4k show codes that contain the required set of relevant information in one code. FIG. 4l shows HIBC code. The HIBC code should be marked in another color than a GS1 code. The medical product should be identified by a HIBC code or a GS1 code. FIGS. 4m and 4n also show HIBC code. It should be able to retrieve the product-ID, lot number and serial number from one single HIBC code.

FIGS. 4o to 4r show non-standardized codes. The code in FIG. 4o must not be used for documentation. The reading device is able to read text to identify which information the codes in FIGS. 4p and 4q contain. FIG. 4r does not contain any computer-readable codes. To process the information in FIG. 4r, the reading device might use text recognition (OCR) or take a photo to document the product. FIG. 4v also does not follow any standards. The information in the figure could be retrieved by OCR or documentation by taking a photo could be possible.

FIGS. 4s to 4u show codes of a sterile material. The reading device can identify that the medical product is a sterile material and retrieve for example an expiry date for the material.

FIGS. 4w and 4x show codes that lead to a website with product information or instructions. The website or the instructions are opened by the reading device and displayed to the user on the displaying device.

Figure 6:
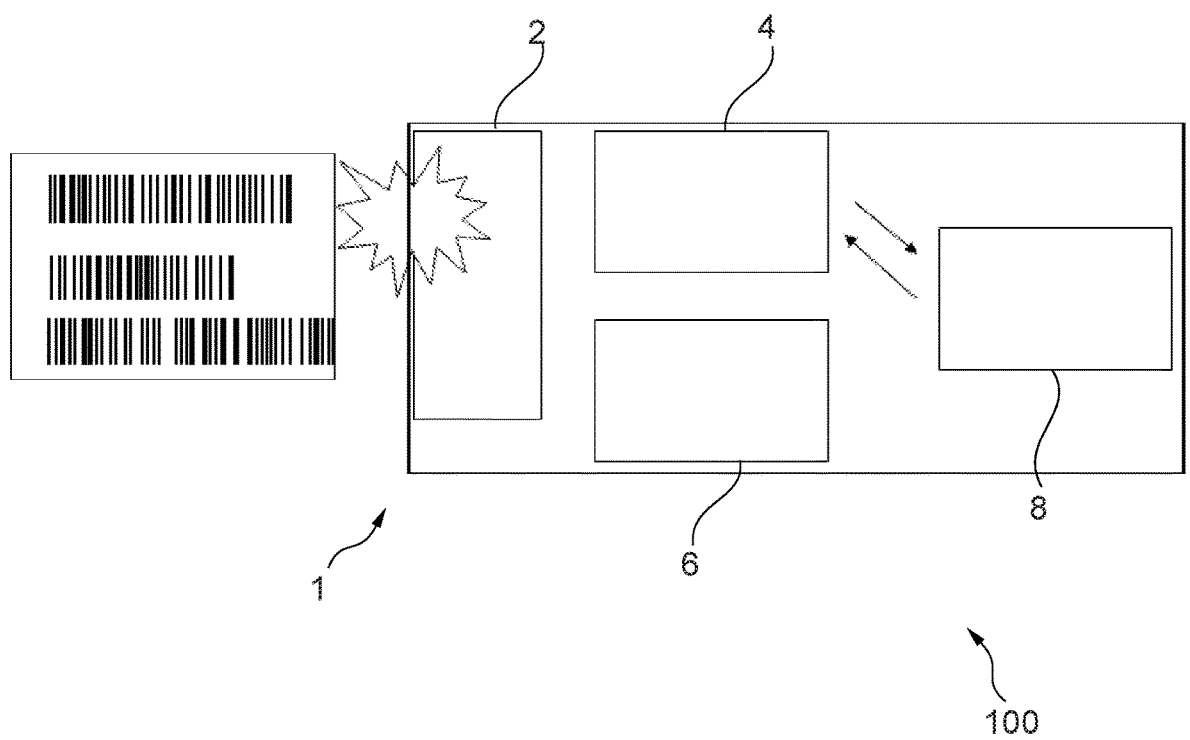
FIG. 6 shows a schematic view of a reading device according to a preferred embodiment of the disclosure.

FIG. 6 shows a schematic view of a reading device 1 according to a preferred embodiment of the present disclosure. The reading device 1 comprises a capturing device 2, an interpretation device 4, a displaying device 6, and a database 8. The capturing device 2 is preferably a camera, especially preferred a smartphone camera. The user or a device uses the capturing device 2 to capture an image of a set of barcodes or scan the set of barcodes. The barcodes are extracted from the captured image or detected in the captured image. The interpretation device 4 decodes the extracted barcodes and detects which product information is stored in the single barcodes. The interpretation device 4 then determines if the predefined set of relevant information is available in the barcodes or in the linked database 8. The interpretation device 4 selects the relevant codes and highlights the relevant codes on the displaying device 6.

Figure 2A:
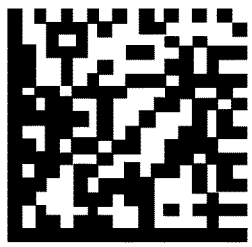
FIGS. 2a to 2g show real-world examples of codes on devices for a better understanding.
Figure 2B:
Figure 2C:
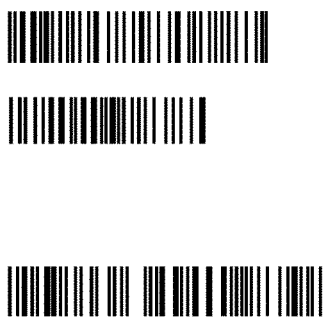
Figure 2D:
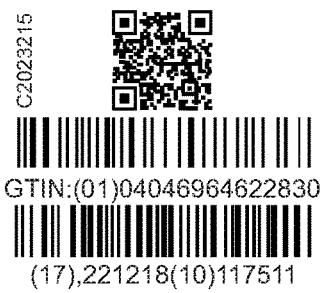
Figure 2E:
Figure 2F:
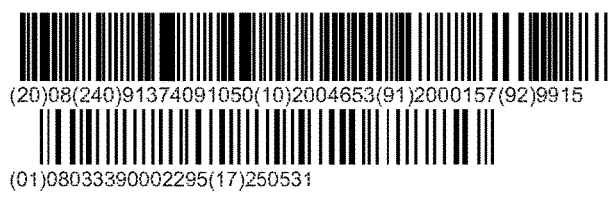
Figure 2G:
Figure 5:
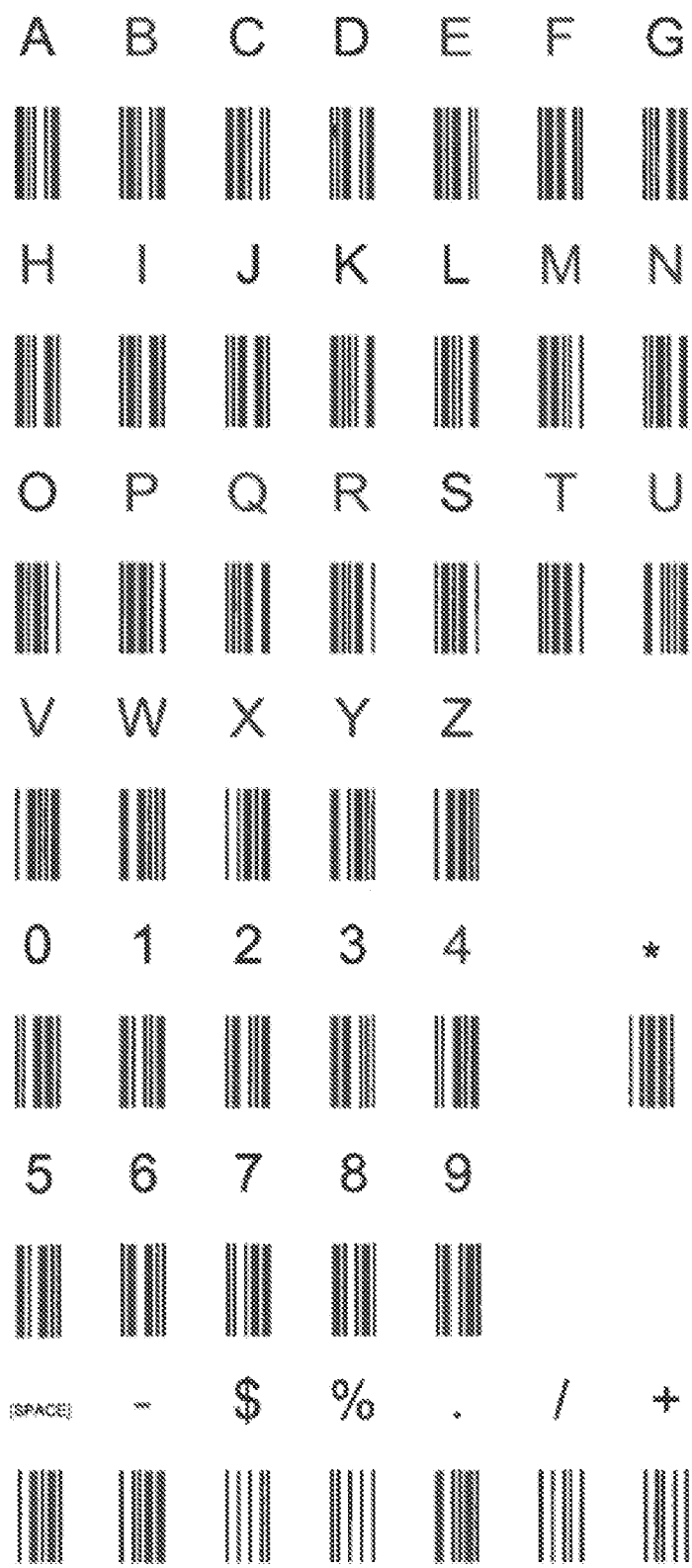
FIG. 5 shows an exemplary barcode decoding table for a better understanding.

In a specific embodiment, the method for capturing multiple computer-readable codes of a medical product or a packaging of a medical product for assisting a user works as explained in the following. The capturing device 2 is a camera, preferably a smartphone camera. The user scans a set of computer-readable codes with the camera. The set of computer-readable codes is for example a set of barcodes as shown in FIGS. 2c and 2d. The camera captures an image of the computer-readable codes. The barcodes are detected in the captured image. The interpretation device 4 decodes the code data stored in the captured barcodes. That means the interpretation device 4 decodes the bars in the barcode for example based on an interpretation table as shown in FIG. 5. The interpretation device 4 further interprets which information is stored in the barcodes.

In the example of FIG. 2c, the interpretation device 4 is able to recognize that the upper barcode contains the product-ID and the middle barcode contains the expiry data and the lot number. The lowest barcode on the other hand contains the product-ID, the expiry data and the lot number. The interpretation device 4 is able to link the medical product to a database by its product-ID and determines if the predefined set of relevant information is provided in the captured barcodes and/or the database. The interpretation device 4 can retrieve the information which product information is necessary to have the complete set of relevant information either from the database 8 or the information is stored in the interpretation device 4. Further product information can be stored in the database 8, for example a sterilization date, a maximum transport or storage time or the like. In this case, the interpretation device 4 would determine that all necessary information are available in the barcodes, as the product-ID, the expiry date and the lot number are provided.

The interpretation device now selects the relevant code or codes. In FIG. 2c the lowest barcode is the relevant code, as it contains all necessary product information and no other code can add information that is not stored in the lowest barcode. Based on the positive determining and the selection of the relevant code, the interpretation device 4 transmits a code marker for every code to the displaying device 6. In this case, the code marker would for example be a green box to mark the lowest code as the relevant code. The two other barcodes would be highlighted by a yellow or orange box to show that the barcodes are valid and conform to the GS1-standard, but are no relevant codes. The user would for example further receive an optical feedback that all relevant information is available and the scanning is complete.

Another example for barcodes is shown in FIG. 2d. The interpretation device 4 would detect in these barcodes that the upper barcode contains the product-ID. That is marked by the (01) identifier according to the GS1-standard. The lower barcode comprises the lot number (10) and the expiry date (17). The interpretation device 4 determines that the predefined set of relevant information is available in the captured barcodes. The determination is therefore positive. The interpretation device 4 selects both barcodes as relevant codes because no barcodes contains all necessary product information alone. The interpretation device 4 therefore combines the information retrieved from the two barcodes to get the predefined set of relevant information. Both barcodes are marked green on the displaying device 6 as a result.

If the interpretation device 4 would determine for a set of barcodes that the predefined set of relevant information is not present in the barcodes, the displaying device 6 would show an alarm or a message to the user that the data is incomplete. The user would further receive a request to scan more barcodes.

Especially, when the reading device is a mobile unit having a camera and a display, the user is able to easily interact with the reading device and user it prior to or while performing a surgery.

Although some aspects have been described in the context of an apparatus, it is clear that these aspects also represent a description of the corresponding method, where a device or a part thereof corresponds to a method step or a feature of a method step. Analogously, aspects described in the context of a method step also represent a description of a corresponding apparatus or part of an apparatus or item or feature of a corresponding apparatus. Some or all of the method steps may be executed by (or using) a hardware apparatus, like for example, a microprocessor, a programmable computer or an electronic circuit. In some embodiments, such an apparatus may execute one or more of the most important method steps.

The invention claimed is:

1. A method for capturing multiple computer-readable codes, of a medical product or a packaging of a medical product for assisting a user, the method comprising the steps of:
    capturing an image of the medical product or its the packaging of the medical product by a capturing device;
    extracting at least a first computer-readable code and a second computer-readable code in the captured image;
    interpreting the first computer-readable code and the second computer-readable code by an interpretation device and retrieving information of at least a product-ID and further product information associated with each of the first computer-readable code and the second computer-readable code;
    determining, based on the retrieved information, whether a predefined set of relevant information for the medical product is included in the information associated with each of the first computer-readable code and the second computer-readable code and/or a linked database,
    selecting the second computer-readable code as a relevant code, when the retrieved information associated with the first computer-readable code is fully included in the retrieved information associated with the second computer-readable code, or selecting the first computer-readable code and the second computer-readable code as the relevant code, if the information associated with the first computer-readable code and the second computer-readable code each includes at least one part of the information of the predefined set of relevant information;

transmitting, based on a result of the determining and on a result of the selecting, a respective code marker for each of the first computer-readable code and the second computer-readable code to a displaying device; and displaying an overlay image with the captured image and, according to the respective code marker, a marking of each of the first computer-readable code and the second computer-readable code for adding assisting visual information to each of the first computer-readable code and the second computer-readable code in order to provide an improved overview of the first computer-readable code and the second computer-readable code to the user.

2. The method according to claim 1, wherein one or more of the respective code markers contains an information that refers to an overlay color and/or a shape around a barcode and/or a text and/or a symbol at or near the respective one of the first computer-readable code and the second computer-readable code.

3. The method according to claim 1, further comprising the steps of:

adding the product information to the database by the interpretation device;

determining, by the interpretation device, whether the database contains the predefined required information;

assigning, if the determination was negative, an alarm or a message to at least one of the respective code markers of the first computer-readable code and the second computer-readable code; and displaying the overlay image with the alarm or message assigned to at least one of the first computer-readable code and the second computer-readable code by the displaying device to the user.

4. The method according to claim 3, further comprising the steps of:

connecting the retrieved product-ID with the database by storing the product-ID in the database or by linking the product-ID of the relevant code to an existing correlated product-ID of the database by the interpretation device;

adding the further product information data to the database of the product-ID by the interpretation device;

determining by the interpretation device, whether the database of the connected product-ID contains the predefined required information.

5. The method according to claim 1, further comprising the steps of:

identifying each one of the first computer-readable code and the second computer-readable code having respective associated information comprising the predefined set of relevant information for the medical product; and displaying the overlay image with a respective green box surrounding each of the first computer-readable code and the second computer-readable code having respective associated information that has been determined to comprise the predefined set of relevant information for the medical product.

6. The method according to claim 1, further comprising the steps of:

identifying each of the first computer-readable code and the second computer-readable code having respective associated information that has been determined to be invalid for not conforming with a supported standard for computer-readable codes; and displaying the overlay image in which each of the first computer-readable code and the second computer-readable code having respective associate information that has been determined to be invalid for not conforming with the supported standard for computer-readable codes is masked/ hidden/ faded out.

7. The method according to claim 1, further comprising the steps of:

assigning at least a part of the at least part of the respective information associated with at least one of the first computer-readable code and the second computer-readable code to the respective code marker of the first computer-readable code and the second computer-readable code; and displaying the part of the respective information in the overlay image next to the respective one of the first computer-readable code and the second computer-readable code in order to assist the user with further information regarding the medical product.

8. The method according to claim 1, wherein the multiple computer-readable codes are barcodes and/or 2D-codes.

9. The method according to claim 1, wherein the capturing device is a smartphone having a camera.

10. The method according to claim 1, wherein the predefined required information is the product-ID, an expiry date and/or a lot number.

11. The method according to claim 1, wherein the product information is an expiry date.

12. A reading device for capturing multiple computer-readable codes of a medical product or a packaging of a medical product for assisting a user, the reading device comprising:

a capturing device configured to capture an image of the medical product or the packaging of the medical product and to extract at least a first computer-readable code and a second computer-readable code in the captured image;

an interpretation device configured to:

interpret the first computer-readable code and the second computer-readable code and retrieve information of at least a product-ID and further product information associated with each of the first computer-readable code and the second computer-readable code, determine, based on the retrieved information, whether a predefined set of relevant information for the medical product is included in the information associated with each of the first computer-readable code and the second computer-readable code and/or a linked database that is stored in a storage unit of the reading device or in a storage unit of a server, select the second computer-readable code as a relevant code, when the information associated with the first computer-readable code is fully included in the information associated with the second computer-readable code; or to select the first computer-readable code and the second computer-readable code as the relevant code, if the information associated with the first computer-readable code and the second computer-readable each includes at least one part of the information of the predefined set of relevant information, and transmit, based on a result of the determining and on a result of the selecting, a respective code marker for each of the first computer-readable code and the second computer-readable code to a displaying device; and a displaying device configured to display an overlay image with the captured image and, according to the respective code marker for each of the first computer-readable code and the second computer-readable code, a marking of the respective one of the first computer-readable code and the second computer-readable code for adding assisting visual information to the respective one of the first computer-readable code and the second computer-readable code in order to provide an improved overview to the user.

13. The reading device according to claim 12, wherein the interpretation device is configured to determine whether information associated with at least one of the first computer-readable code and the second computer-readable code conforms with a GS-1-standard and that another GS1-standard barcode should be available to be captured, and if the determination is positive, the displaying device displays feedback to the user to capture another computer-readable code.

14. The reading device according to claim 12, wherein the interpretation device comprises text recognition and is configured to link at least one of the first computer-readable code and the second computer-readable code to a description that is not defined in the first computer-readable code or the second computer-readable code.

15. The reading device according to claim 12, wherein the interpretation device is configured to determine whether information associated with at least one of the first computer-readable code and the second computer-readable code belongs to a sterile material and when the determination is positive, the interpretation device retrieves additional information about the sterile material from the database.

16. The reading device according to claim 12, wherein the interpretation device is adapted to, upon determining that not all information of the set of predefined relevant information included in the information associated with each of the first computer-readable code and the second computer-readable code, interrupt a functionality of an associated electrically powered medical product and display an alarm to the user by the displaying device.

17. The reading device according to claim 12, wherein the interpretation device has a predefined set of selectable code markers stored in the storage unit, wherein the code marker contains an information that refers to an overlay color and/or a shape around the barcode and/or a text and/or a symbol at or near the respective code.

18. The reading device according to claim 15, wherein the additional information about the sterile material is an expiry date.

19. The reading device according to claim 16, wherein the functionality of the medical product is a power supply.

20. The reading device according to claim 12, further comprising
a central server device having a storage with a database, the server being connected with the at least one reading device for transferring data to and from the at least one reading device.

21. A computer-readable storage medium comprising instructions which, when executed by a computer, cause the computer to carry out a method comprising:
capturing an image of a medical product or a packaging of the medical product by a capturing device;
extracting at least a first computer-readable code and a second computer-readable code in the captured image;
interpreting the first computer-readable code and the second computer-readable code by an interpretation device and retrieving information of at least a product-ID and further product information associated with each of the first computer-readable code and the second computer-readable code;
determining, based on the retrieved information, whether a predefined set of relevant information for the medical product is included in the information associated with each of the first computer-readable code and the second computer-readable code and/or a linked database,
selecting the second computer-readable code as a relevant code, when the retrieved information associated with the first computer-readable code is fully included in the retrieved information associated with the second computer-readable code, or selecting the first computer-readable code and the second computer-readable code as the relevant code, if the information associated with the first computer-readable code and the second computer-readable code each includes at least one part of the information of the predefined set of relevant information;
transmitting, based on a result of the determining and on a result of the selecting, a respective code marker for each of the first computer-readable code and the second computer-readable code to a displaying device; and
displaying an overlay image with the captured image and, according to the respective code marker, a marking of each of the first computer-readable code and the second computer-readable code for adding assisting visual information to each of the first computer-readable code and the second computer-readable code in order to provide an improved overview of the first computer-readable code and the second computer-readable code to the user.

* * * * *